United States Patent
Däscher et al.

(10) Patent No.: US 7,040,318 B2
(45) Date of Patent: May 9, 2006

(54) VENTILATOR

(75) Inventors: Jakob Däscher, Buchs (CH); Michael Griffiths, Carlsbad, CA (US)

(73) Assignees: IMT Medical AG, Liechtenstein (IE); Event Medical Ltd., Liechtenstein (IE)

( * ) Notice: Subject to any disclaimer, the term of this patent is extended or adjusted under 35 U.S.C. 154(b) by 0 days.

(21) Appl. No.: 10/484,120

(22) PCT Filed: Jul. 30, 2001

(86) PCT No.: PCT/IB01/01362

§ 371 (c)(1),
(2), (4) Date: Jul. 16, 2004

(87) PCT Pub. No.: WO03/013635

PCT Pub. Date: Feb. 20, 2003

(65) Prior Publication Data

US 2004/0244795 A1    Dec. 9, 2004

(51) Int. Cl.
*A61M 16/00* (2006.01)

(52) U.S. Cl. .......................... 128/204.21; 128/204.22; 128/204.23; 128/204.18

(58) Field of Classification Search ........... 128/204.21, 128/204.22, 204.23, 204.18
See application file for complete search history.

(56) References Cited

U.S. PATENT DOCUMENTS

| 5,954,050 A | 9/1999 | Christopher | 128/204.23 |
| 6,003,070 A | 12/1999 | Frantz | 709/206 |
| 6,024,089 A * | 2/2000 | Wallace et al. | 128/204.21 |
| 6,305,372 B1 * | 10/2001 | Servidio | 128/204.21 |

FOREIGN PATENT DOCUMENTS

| WO | 00 42911 A | 7/2000 |
| WO | 00 59566 A | 10/2000 |
| WO | 01 24690 A | 4/2001 |
| WO | 01 32069 A | 5/2001 |

* cited by examiner

*Primary Examiner*—Mital Patel
(74) *Attorney, Agent, or Firm*—Kaplan Gilman Gibson & Dernier LLP

(57) ABSTRACT

A novel ventilator, which can be operated from main power, an internal or external battery supply, includes an integral compressor, valves, sensors, and embedded web server. The embedded web server can be connected to external monitoring devices.

15 Claims, 1 Drawing Sheet

*Fig. 1*

VENTILATOR

TITLE OF THE INVENTION

The invention refers to a ventilator according to the generic term of claim no. 1.

BACKGROUND OF THE INVENTION

Ventilators and other respiratory support devices are used to either ventilate patients who have breathing difficulties or an inability to breath on their own, or they are used as gas mixing devices to condition the delivery and the gas mixture inhaled by a patient. They therefore have gas connections, valves and controls for the valves, to create appropriate gas mixtures to deliver into the patient's breathing circuit, airways, and lungs.

DETAILED DESCRIPTION OF THE INVENTION

Figure 1:
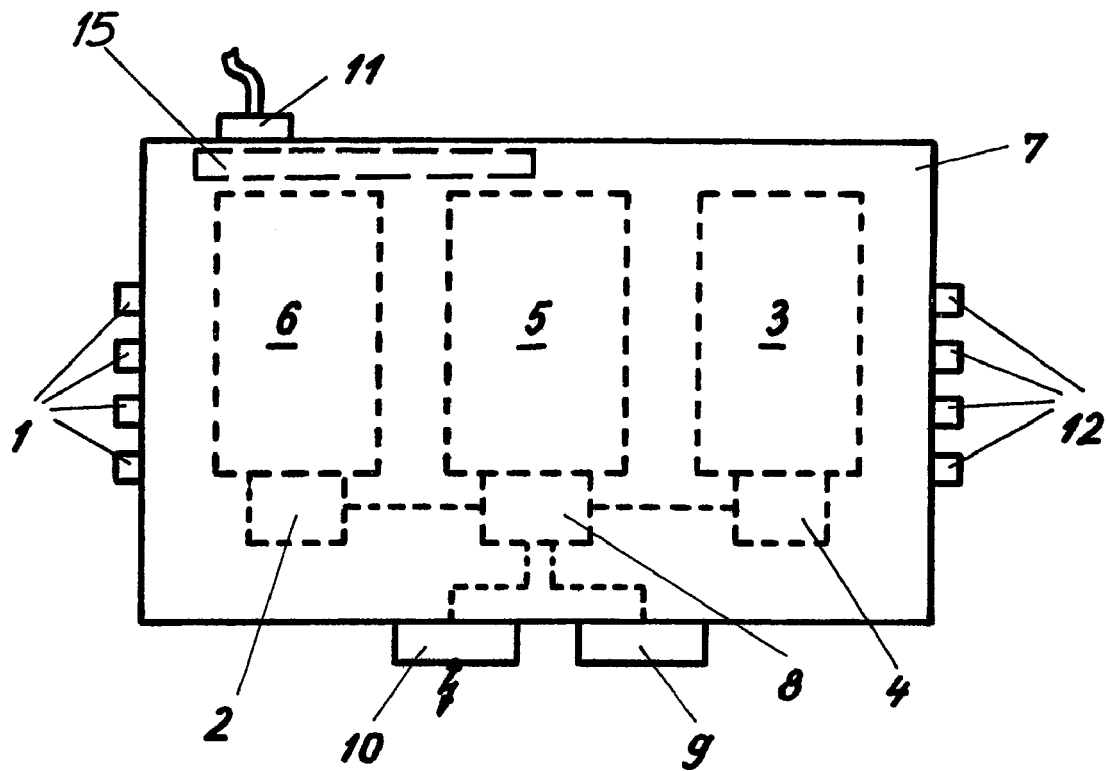
FIG. 1 is a block diagram of one embodiment of the present invention.
Figure 1:
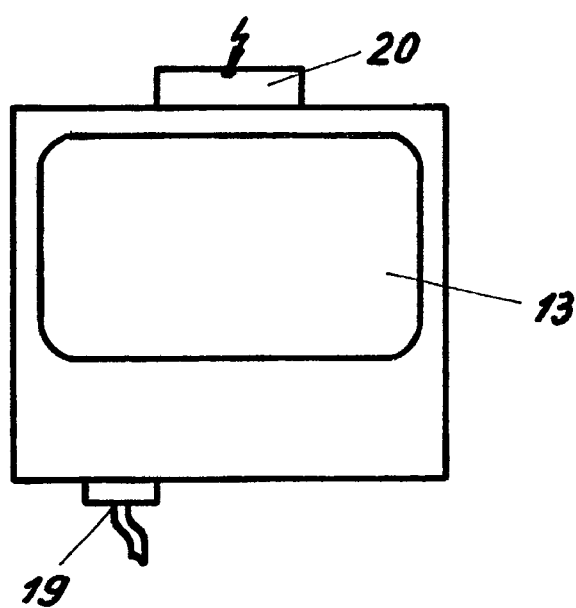

The applicants have put one of the most modern and highly developed ventilators in existence on the market bearing the name INSPIRATION. This well-known device and variations of the same have been placed under protection as described by the published PCT patent application WO-A-00/59566.

Ventilators are often operated automatically and are routinely checked by care staff. Critically ill patients are additionally monitored by pulse, cardiac and blood pressure equipment to ensure that any critical situations are recognized in good time and action can be taken. Video surveillance, or similar methods, may also be used. However these widely used methods tend to concentrate on displaying the resultant external effects to the patient of a malfunction in the ventilator or a problem in the patient's breathing.

In contrast to this, the invention aims to find a way to be able to check the ventilator's performance, or the breathing performance of the patient being treated by the ventilator, directly on the device and in real time.

This task is solved by integrating additional sensors and/or tapping into the existing sensors in the ventilator using an embedded web server, which can be output to external monitors via an Ethernet output, via a data-only connection and/or via the Internet, allowing the current ventilator and patient status to be directly polled or permanently observed at any time.

The embedded web server has it's own computer. It comes preloaded with a software program, which can be used to display a homepage via an external data connection, which permits viewing of, and alteration to the functions and performance parameters of the ventilator.

A device equipped in this manner therefore offers improved patient safety. At the same time, staffing requirements can be reduced, as the monitoring can also take place from more remote locations and staff need only be called upon in an emergency.

The invention is specially designed to include a GSM or UMTS connection and appropriate send/receive unit in the embedded web server, so that monitoring is not dependent on a cable network. This is of particular benefit if the ventilator, equipped in this preferred way, is also to be operated by battery, independent of mains power (please compare the details given on this in the applicant's WO-A mentioned).

To achieve complete electrical self-sufficiency, where all electrically operated parts, which also includes the internal gas compressor, the electronics and the send/receive equipment, can be supplied with power from an internal battery. This battery should ideally be the main source of energy and should only be given a constant mains boost or charge via a charger where a mains feed is available. With this invention, disconnecting from the mains supply will not therefore interrupt ventilation or ventilation monitoring in any way.

An integrated charger, as well as supplementary connections as appropriate, are preferably available, as detailed in the WO-A. No further details shall therefore be given here, as the expert can refer to the WO-A for all relevant information.

The ventilator also includes special, new and independently applicable software, which allows forced sigh ventilation to be set for any interval and any pressure and/or volume value. Sigh ventilation of this sort can therefore be optimally monitored, varied or deactivated from a distance.

The invention includes the provision of generally known passwords and software-supported access controls in the embedded web server for all device interventions.

DESCRIPTION OF A SAMPLE PREFERRED DESIGN

The figure describes a sample preferred design for the invention as a block diagram. It provides an example and is not restrictive.

The attached list of components, as well as the technical information contained in the patent claims, form part of the description disclosed herein. Additional benefits and features of the invention, as well as additional preferred formations, arise from the description of the figure.

The functionality and design of the preferred sample design can be seen in the block diagram: on the input side you will see the gas connections 1, as well as the compressor input, compressed air input, ventilation gas input, e.g. for oxygen and any therapy gas required, e.g. for NO. The inputs are sited on a block, which is found within the housing 7. Also inside the housing 7 you will find a compressor 6 with controllable valves or similar, and a control system for this. Housing 7 also contains measuring sensors 3, which are connected to control system 2 or their own control system 4.

Finally, the invention includes a new embedded web server 5 inside the housing 7, which also has a control system 8. It communicates with control systems 2 and 4 to exchange and make available any relevant information.

Data outputs 9 and 10 are connected to the embedded web server 5 or its control system 8. On the one hand, they provide connection to a data network (e.g. telephone network or internal company Ethernet) and/or connection to a GSM or UMTS network.

On the input side, the device has a power connection 11, which is connected inside the housing 7 to power storage devices 15 (e.g. storage batteries), which are not shown in more detail.

On the output side, patient connections 12 are indicated, which represent on the one hand the ventilation gas supply, but on the other hand are also measuring lines leading to the patient's mouthpiece and/or to the patient or to sensors, which are attached to the patient, as is generally understood.

For details on the possible design of a device complying with this invention, please refer to the applicant's WO-A, in particular the figures and description of figures, which applies as if it were disclosed herein.

LIST OF COMPONENTS

1 Gas connections
2 Control system
3 Measuring sensors
4 Control system
5 Embedded web server
6 Compressor
7 Housing
8 Control system
9 Data output to a cable network
10 Data output to GSM, UMTS, or similar
11 Power connection
12 Patient connections
13 Monitor
19 Power connection
20 Receiver

What is claimed is:

1. A ventilator, comprising:
a housing;
a compressor located within said housing, said compressor having a first control system for controlling its operation;
a multiple of measuring sensors located within said housing, said measuring sensors having a second control system for controlling their operation; and
a web server located within said housing and connected to at least said first or second control system, said web server providing a connection to an external monitor via at least one data output.

2. A ventilator as described in claim 1, wherein the data output includes send/receive equipment, which is connectable to either an Ethernet, and/or radio GSM and/or UMTS networks.

3. A ventilator as described in claim 2, wherein operating software of the ventilator can be downloaded and updated via the send/receive equipment.

4. A ventilator as described in claim 1, wherein the embedded web server is equipped with software operable to cause ventilator functions, monitored patient data, including graphical loops and waveforms, and settings to be displayed on a website, and to permit these functions and settings to be called up and altered via the website.

5. A ventilator as described in claim 4, wherein access to the server or website is protected by both password and hardware encryption.

6. A ventilator as described in claim 4, wherein the control system has software that is operable to permit sigh ventilation to be set and monitored for a patient using any time intervals and any pressures and/or volume values, and to permit adjustments thereof via the website.

7. A ventilator as described in claim 1, wherein sensor measurements from sensors at the patient can be interfaced to the embedded web server via the patient connection.

8. A ventilator as described in claim 1, further comprising an internal power supply, including a storage battery located inside the housing and coupled to the electrical control systems, the compressor, and the embedded web server, wherein the input of the power supply is connected to an output of at least one integrated charger, and the charger receives its input from at least two different sources of power feed.

9. A ventilator as described in claim 1, wherein diagnostic and service data can be viewed and managed remotely via a website of an embedded web server.

10. A ventilator as described in claim 1, wherein software provides a program that permits the ventilator, via the embedded web server, to email a service technician when preventive maintenance or repairs are required.

11. A ventilator as described in claim 1, wherein: the embedded web server is operable to maintain a website, and the control system has software that is operable to permit sigh ventilation to be set, monitored and adjusted via the website for a patient using any time intervals and any pressures and/or volume values.

12. A ventilator as described in claim 1, wherein the embedded web server is operable to maintain a website, and at least one of the controlled valve and the controlled compressor may be at least partially controlled via the website.

13. A ventilator as described in claim 1, wherein the embedded web server is operable to maintain a website, and at least some patient data obtained via the patient connection is available via the website.

14. A ventilator as described in claim 1, wherein the embedded web server is operable to maintain a website, and at least some data concerning ventilator functions or settings is available via the website.

15. The ventilator as described in claim 1, wherein said first and second control systems are implemented as a single system.

* * * * *